(12) United States Patent
Tsujita

(10) Patent No.: US 6,687,534 B2
(45) Date of Patent: Feb. 3, 2004

(54) FLUORESCENT-LIGHT IMAGE DISPLAY APPARATUS

(75) Inventor: Kazuhiro Tsujita, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 371 days.

(21) Appl. No.: 09/919,613

(22) Filed: Aug. 1, 2001

(65) Prior Publication Data

US 2002/0016620 A1 Feb. 7, 2002

(30) Foreign Application Priority Data

Aug. 1, 2000 (JP) ....................................... 2000-232903

(51) Int. Cl.[7] ................................................ A61B 6/00
(52) U.S. Cl. ....................... 600/476; 600/477; 600/321; 600/317
(58) Field of Search ................................ 600/476, 477, 600/321, 317, 160; 348/65

(56) References Cited

U.S. PATENT DOCUMENTS

| | | | |
|---|---|---|---|
| 5,507,287 A | * | 4/1996 | Palcic et al. ................. 600/317 |
| 6,364,829 B1 | * | 4/2002 | Fulghum .................... 600/160 |
| 6,462,770 B1 | * | 10/2002 | Cline et al. .................... 348/65 |
| 6,498,948 B1 | * | 12/2002 | Ozawa et al. ................ 600/476 |
| 6,516,217 B1 | * | 2/2003 | Tsujita ........................ 600/477 |

* cited by examiner

*Primary Examiner*—George Manuel
*Assistant Examiner*—Ruby Jain
(74) *Attorney, Agent, or Firm*—Sughrue Mion, PLLC

(57) ABSTRACT

A fluorescent-light image display apparatus for displaying on a monitor a fluorescent-light image emitted from a target area irradiated by a excitation light. A photo-detector inputs the output value of the excitation light into an irregularity controller, which determines whether or not the output of the excitation light is smaller than a set value. If the output of the excitation light is determined to be larger than the set value, an irregularity detection signal is output to the main controller. The main controller stops the flow of drive-current to and the emission of excitation light from the GaN semiconductor laser, and displays a message on the monitor that an irregularity has occurred in the output of the excitation light when the output of the excitation light is larger than a predetermined value, the emission of the excitation light is stopped and the patient is not irradiated by excitation light having an energy density above a predetermined value.

16 Claims, 8 Drawing Sheets

F I G . 8
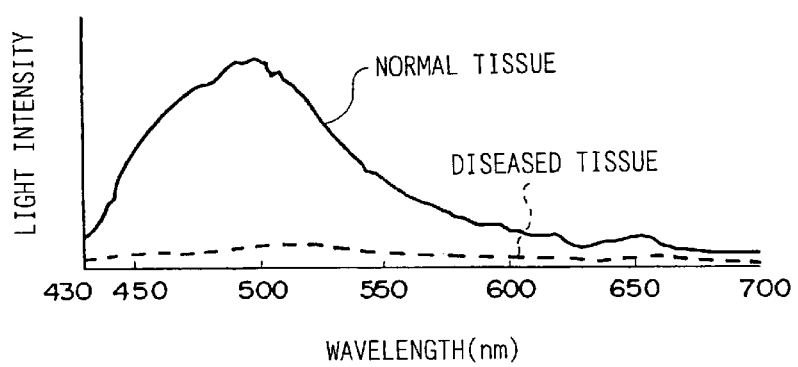

FLUORESCENT-LIGHT IMAGE DISPLAY APPARATUS

BACKGROUND OF THE INVENTION

1. Field of the Invention

The present invention relates in general to a fluorescent-light image display apparatus for displaying a fluorescent-light image obtained of the fluorescent-light emitted from a fluorescent drugs (extrinsic fluorophores) that has been injected in advance into an examination area of a living tissue subject (hereinafter target subject) upon irradiation thereof by a excitation light, or a fluorescent-light image obtained of the autofluorescent-light emitted from the intrinsic fluorophores of a target subject, into which a fluorescent drugs (extrinsic fluorophores) has not been injected, upon irradiation thereof by a excitation light.

2. Description of the Related Art

There are known in the field of fluorescent-light image diagnostic apparatuses for displaying a fluorescent-light image based on the fluorescent-light emitted from an examination area of a target subject upon irradiation thereof by a excitation light having a wavelength within the wavelength range of the intrinsic fluorophores of aforementioned target subject or a fluorescent-light image based on the fluorescent-light emitted from a fluorescent drugs (extrinsic fluorophores), which has been injected in advance into a target subject under examination, upon irradiation thereof by a excitation light.

For example, technologies have been proposed that make use of the fact that the intensity of the fluorescent-light emitted from a normal tissue differs from the intensity of the fluorescent-light emitted from a diseased tissue when a target subject is irradiated by a excitation light having a wavelength within the wavelength range of the intrinsic fluorophores of the target subject, wherein, by receiving the fluorescent-light emitted from a target subject upon irradiation thereof by a excitation light having a wavelength within the wavelength range of the intrinsic fluorophores of the target subject, the location and range of penetration of a diseased tissue is displayed as a fluorescent-light image.

Normally, when a target subject is irradiated by a excitation light, because a high-intensity fluorescent-light is emitted from a normal tissue, as shown by the solid line in FIG. 8, and a weak-intensity fluorescent-light is emitted from a diseased tissue, as shown by the broken line in FIG. 8, by measuring the intensity of the fluorescent-light emitted from aforementioned target subject, it can be determined whether the target subject is in a normal or a diseased state.

However, for cases in which the intensity of the fluorescent-light emitted from a target subject upon irradiation thereof by a excitation light is displayed as an image, because there is unevenness on the surface of a target subject, the intensity of the excitation light irradiating the target subject is not of a uniform intensity. Further, although the intensity of the fluorescent-light emitted from the target subject is substantially proportional to the intensity of the excitation light, the intensity of aforementioned fluorescent-light becomes weaker in inverse proportion to the square of the distance between the excitation light and the target subject. Therefore, there are cases in which the fluorescent-light received from diseased tissue located at a position closer to the excitation light source than normal tissue is of a higher intensity than the fluorescent-light received from normal tissue located further from said light source, and the state of the tissue of the target subject under examination cannot be accurately recognized based solely on the data relating to the intensity of the fluorescent-light received from the target subject upon irradiation thereof with a excitation light. In order to remedy the problems described above, the applicants of the present application propose a method of displaying a fluorescent-light image obtained based on the factor obtained by dividing the ratio of two types of fluorescent-light intensities obtained of different wavelength ranges. That is to say: an image display method of displaying an image based on the difference in the form of the fluorescence spectra reflecting the tissue-state of a target subject; a method of displaying a fluorescent-light image comprising the steps of: irradiating a target subject with a reference light in the near-infrared spectrum, which shows uniform absorption characteristics for a wide variety of target subjects; detecting the intensity of the reflected light reflected by said target subject; determining the ratio between the intensity of said reflected light and fluorescent light intensity by division; and displaying a fluorescent light image based on the factor of said division, among others.

In addition, fluorescent-light image display methods wherein the hue, which is one of the three color properties, is determined based on the ratio between aforementioned two intensities of fluorescent-light or the ratio between the intensity of the reflected-light of the reference-light and the intensity of the fluorescent-light, and the luminosity, which is one of the three color properties, is determined based on the intensity of the reflected-light of the reference-light and the fluorescent-light image is displayed, etc., are being developed.

Further, the fluorescent-light image display apparatus based on the technology described above comprises a excitation light emitting means for projecting excitation light, an illuminating-light emitting means for projecting illuminating-light, a fluorescent-light image display means for displaying a fluorescent light image obtaining means which images the fluorescent light emitted from an examination area which has been irradiated by a excitation light, a reflectance image obtaining means which images the reflected light reflected by said examination area which has been illuminated by an illuminating light, a fluorescent light image display means which displays a fluorescent light image, and a reflectance image display means which displays a reflectance image, wherein these types of fluorescent-light image obtaining means are in many cases provided in the configuration of an endoscope for insertion into a body cavity of a patient, a colposcope, or a surgical microscope.

According to the conventional fluorescent-light image obtaining apparatuses described above, in order to ensure the safety of a patient, the output of the excitation light is set so that the density of the energy of the excitation light projected onto the area under examination is smaller than an MPE value determined according to the JIS safety standard. On the other hand, the fluorescent-light emitted from an area under examination that has been irradiated by the excitation light is extremely weak, and in order to obtain a fluorescent-light image having a good S/N ratio, because it is desirable that the output of the excitation light be as large as possible, it is often the case that the output of the excitation light is set so that the energy density of the excitation light is a value only slightly smaller than the MPE value.

Because of this, for cases in which there is an irregularity with regard to an increase in the output of the excitation light emitted by the excitation light emitting means of a conventional fluorescent-light image obtaining apparatus, the output of the excitation light exceeds the set value, and there is a fear that the target subject will be irradiated by a excitation light having an energy density larger than the predetermined value.

SUMMARY OF THE INVENTION

The present invention has been developed in consideration of the circumstances described above, and it is a primary object of the present invention to provide a fluorescent-light image display apparatus in which there is no projection onto an area under examination of excitation light having an energy level larger than a predetermined value, even for cases in which there is an irregularity regarding an increase in the output of the excitation light, whereby the safety of the apparatus is improved.

The fluorescent-light image display apparatus according to the present invention comprises a excitation light emitting means for emitting excitation light, an illuminating-light emitting means for emitting reference-light, a fluorescent-light image obtaining means for obtaining an image formed by the fluorescent-light emitted from an examination area of a target subject upon the irradiation thereof by the excitation light, a reflectance image obtaining means for obtaining a reflectance image formed by the reflected-light reflected from an examination area of a target subject upon the irradiation thereof by the reference-light, a fluorescent-light image display means for displaying a fluorescent-light image based on a fluorescent-light image, and a reflectance image displaying means for displaying a reflectance image based on the reflectance image, wherein the excitation light emitting means is provided with an irregularity detecting means for detecting irregular increases occurring in the output of the excitation light, and a excitation light emission stopping means for stopping the emission of the excitation light being projected onto a target subject under examination, according to the detection of an irregularity by the irregularity detecting means.

Here, "a fluorescent-light image based on a fluorescent-light image" can refer to: any type of fluorescent-light image formed based on at least one type of fluorescent-light image; and more specifically, to a fluorescent-light image based on the ratio between two types of fluorescent-light images or a fluorescent-light image based on the ratio between a fluorescent-light image and an IR reflected-light image formed of the reflected-light of a near-infrared light; or a fluorescent-light image for which the hue has been determined based upon the ratio between two types of fluorescent-light images and the brightness has been determined based upon an IR reflected-light image.

In addition, the fluorescent-light image display apparatus according to the present invention can further comprise a switching means capable of switching, by use of an input operation, between a fluorescent-light image display and viewing mode, in which the excitation light is projected onto an examination area of a target subject and a fluorescent-light image obtained, and a reflectance image display and viewing mode, in which the illuminating-light is projected onto a target subject under examination and a reflectance image obtained, and a reflectance image viewing mode setting means for switching from the fluorescent-light image viewing mode to the reflectance image viewing mode when an irregularity is detected by the irregularity detecting means while the apparatus is in the fluorescent-light image viewing mode.

Further, the fluorescent-light image display apparatus according to the present invention can be further provided with an irregularity notification means for providing notification that an irregularity has occurred, corresponding to the detection of an irregularity by the irregularity detecting means.

Here, "an irregularity notification means for providing notification that an irregularity has occurred" can refer to any type of means that provides notification to an operator that an irregularity has occurred; more specifically, a message indicating that an irregularity has occurred can be displayed on the display means, a buzzer or other warning sound can be sounded, etc.

A means that can detect that the excitation light emitted from the excitation light emitting means or the output of emitted light having an output corresponding to the output of the excitation light is greater than a predetermined value can be used as the irregularity detecting means.

Further, if the excitation light emitting means is a means provided with a excitation light source for producing excitation light and a drive means for providing drive-current to said excitation light source, a drive-current detecting means for detecting that the drive current is greater than a predetermined value can be used as the irregularity detecting means.

If the excitation light emitting means is a means provided with a excitation light source for increasing the output of the emission of excitation light if the temperature falls and a temperature regulating means for adjusting the temperature of said excitation light source, a temperature detecting means for detecting that the temperature of the excitation light source is below a predetermined value can be used as the irregularity detecting means.

The irregularity detecting means can be a means provided with at least two detecting means from among the emission-output detecting means, the drive-current detecting means, and the temperature detecting means described above.

If the excitation light emitting means is a means provided with a excitation light source for producing excitation light and a drive means for supplying drive-current to said excitation light source, a drive stopping means for stopping the supply of drive-current to the excitation light source can be used as the excitation light emission stopping means.

Further, an optical path cutoff means for cutting off the optical path between the excitation light emitting means to and an examination area of a target subject, of the excitation light can be used as the excitation light emission stopping means.

As to the wavelength band of the excitation light, a wavelength band in the range of 400–420 nm can be used. Further, a semiconductor laser can be used as the excitation light source; in particular, it is preferable that a GaN semiconductor laser is used.

According to the fluorescent-light image display apparatus of the configuration described above according to the present invention, when an irregular increase in the output of the excitation light occurs, because the emission of excitation light onto the target area is stopped, the patient is not irradiated with excitation light having an energy density above a predetermined value, and the safety of the fluorescent-light image display apparatus is improved.

In addition, for cases in which a fluorescent-light image display apparatus provided as part of an endoscope apparatus, etc. that switches between a fluorescent-light image viewing mode, in which a target subject is irradiated with a excitation light, a fluorescent-light image formed of the fluorescent-light emitted from the target subject upon irradiation thereof by the excitation light is obtained and a fluorescent-light image based on the fluorescent-light image is displayed, and a reflectance image display mode, in which a target subject is illuminated with an illuminating-light, a reflectance image formed of the reflected-light of the illuminating-light reflected from the target subject upon illumination thereof by the illuminating-light is formed, and a reflectance image based on the reflectance image is displayed, and displays a fluorescent-light image or a reflectance image is used: first, in the reflectance image viewing mode, while viewing a reflectance image displayed on the display, etc., an operator inserts the insertion portion of the endoscope apparatus into the portion of the body of the patient near the location of the area under examination; after which, the operator switches to the fluorescent-light image viewing mode and the obtaining and displaying of a fluorescent-light image is performed; and after viewing of said fluorescent-light image has been completed, the operator again switches to the reflectance image viewing mode, and while viewing the displayed reflectance image, removes the insertion portion of the endoscope apparatus from the body of the patient. Therefore, if the emission of the excitation light stops while in the fluorescent-light image viewing mode, interference occurs in the fluorescent-light image appearing on the display, and there are cases for which an operator cannot clearly view the examination area of a target subject.

According to the fluorescent-light image display apparatus of the present invention, a fluorescent-light image viewing mode and a reflectance image viewing mode are switched between and viewing is performed, and by stopping the emission of the excitation light and automatically switching to the reflectance image viewing mode when an irregularity occurs in the excitation light emitting means, a reflectance image is displayed instead of the fluorescent-light image of the examination area of a target subject. Therefore, even if an irregularity occurs in the excitation light emitting means, a patient is not irradiated with excitation light having an energy density above a predetermined value, and furthermore, because an operator can continue to view the examination area of a target subject, the safety level can be improved even for a fluorescent-light image display apparatus in which a fluorescent-light image viewing mode and a reflectance image viewing mode are switched between and viewing is performed.

For cases in which an irregularity occurs in the excitation light emitting means, because notification indicative thereof is provided to the operator, the operator can take appropriate measures, and the safety level of the apparatus is thereby improved a level.

If an emission-output detecting means for detecting that the output of the excitation light is above a setting value is used as the irregularity detecting means, the emission of the excitation light can be stopped when the output thereof is detected to be above a predetermined value.

If a drive-current detecting means for detecting that the drive-current supplied to the excitation light source is above a predetermined value is used as the irregularity detecting means, for cases in which excessive drive-current is supplied to the excitation light source, that is, for cases in which the possibility that the output of the excitation light will increase is great, the emission of the excitation light can be stopped.

If a temperature detecting means for detecting that the temperature of the excitation light source is below a predetermined value is used as the irregularity detecting means, for cases in which an irregularity occurs in the temperature regulating means and the excitation light source has been excessively cooled, that is, when there is a fear that the output of the excitation light will increase, the emission of the excitation light can be stopped.

For cases in which at least two detecting means from among an emission-output detecting means, a drive current detecting means and a temperature detecting means are provided, even if one of the detecting means malfunctions, because an irregularity in the excitation light means can be detected by the other, properly functioning detecting means, the emission of the excitation light can reliably be stopped when an irregularity occurs.

Further, by using excitation light of a wavelength within the 400–420 nm wavelength range, more reliable data of the target subject can be obtained. Also, by using a GaN semiconductor laser as the excitation light source, it is possible to make the apparatus more compact, and to reduce cost.

BRIEF DESCRIPTION OF THE DRAWINGS

FIG. 8 is a drawing provided for the explanation of the ratio of the distribution of the intensity of the fluorescence spectra of fluorescent-light.

DESCRIPTION OF THE PREFERRED EMBODIMENTS

Figure 1:
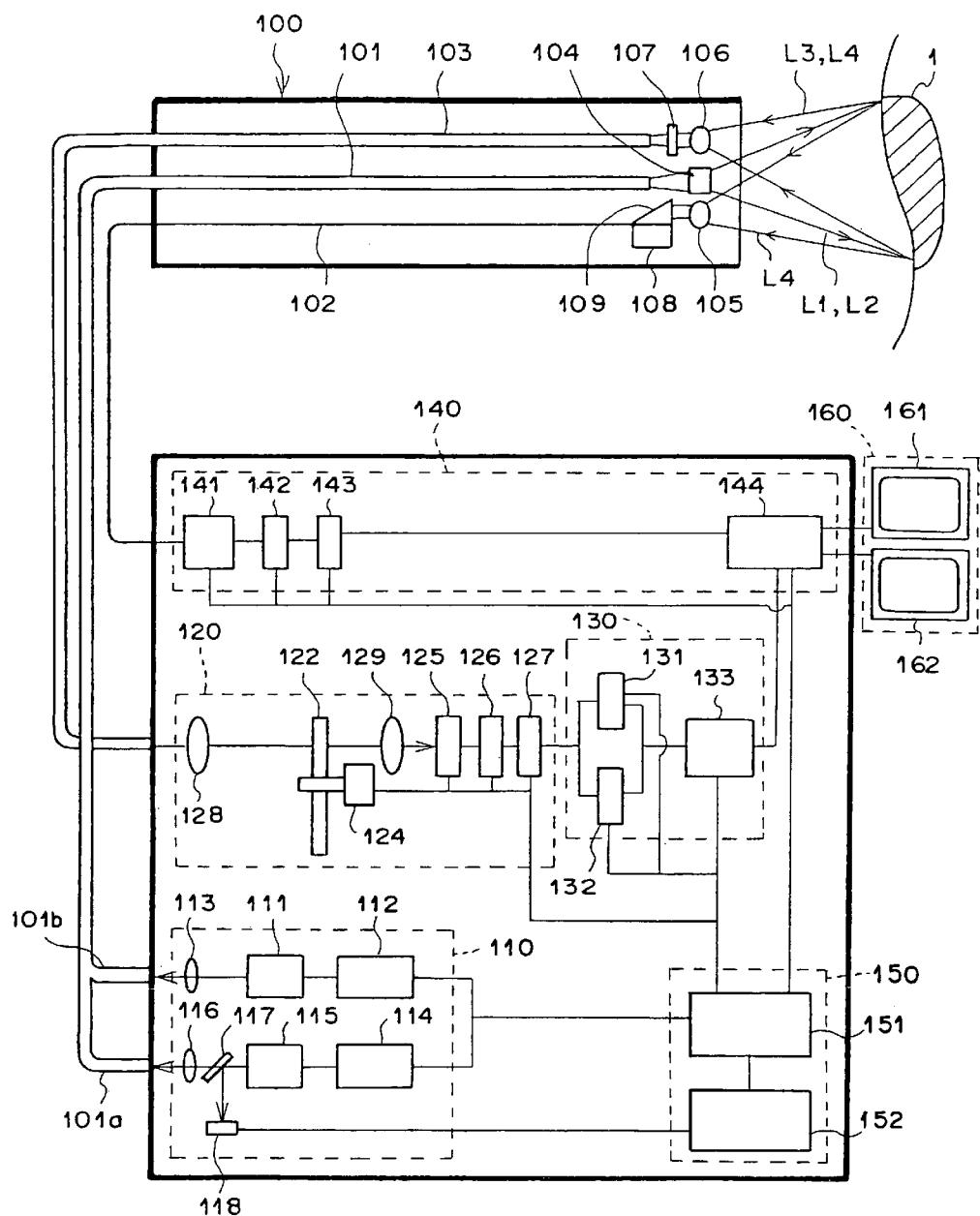
FIG. 1 is a schematic drawing of the first embodiment of a fluorescence endoscope apparatus implementing the fluorescent-light image display apparatus according to the present invention.

Hereinafter, with reference to the drawings, the preferred embodiments of the present invention will be explained. First, referring to FIGS. 1 and 2, the first embodiment of a fluorescence endoscope apparatus implementing the fluorescent-light image display apparatus according to the present invention will be explained. FIG. 1 is a schematic drawing of the first embodiment of a fluorescence endoscope apparatus implementing the fluorescent-light image display apparatus according to the present invention. According to the fluorescence endoscope apparatus of the current embodiment: a narrow-band fluorescent-light image and a wide-band fluorescent-light image are obtained from the fluorescent-light L3 emitted from a target subject 1 upon irradiation thereof by a excitation light L2, and a hue signal determining a hue H occurring in the Munsell color specification system is formed based on the factor of the light-intensity of both images; an IR reflected-light image is obtained from the reflected-light L4 reflected from the target subject 1 upon irradiation thereof by a white-light L1, and a brightness signal determining a luminosity V occurring in the Munsell color specification system is formed based on the light-intensity of the IR reflected-light image; and a fluorescent-light image combining both signals is displayed on a display 162, wherein; the output of the excitation light L2 is regularly monitored, and when the output of the excitation light L2 exceeds a predetermined value, the emission of the excitation light L2 is stopped and notification indicative thereof is provided to the operator.

The fluorescence endoscope apparatus according to the current embodiment of the present invention comprises: an endoscope insertion portion 100 to be inserted into the body of a patient to a position near the location of the primary nidus and areas of suspected secondary infection; an illuminating unit 110 provided with alight source that emits white-light L1 for obtaining standard and IR reflected light images and excitation light L2 for obtaining fluorescent-light images; an image obtaining unit 120 for obtaining two types of fluorescent-light images of different wavelength ranges and an IR reflected-light image; a fluorescent-light image forming unit 130 for computing a factor of said two types of fluorescent-light images and obtaining a hue signal based on said factor, and obtaining a brightness signal based on the light-intensity of the IR reflected-light image and forming a fluorescent-light image based on both of said signals; an image processing unit 140 for performing the image processing for displaying a fluorescent-light image and a reflectance image as visible images; a control unit 150 for controlling the operation timing, control in the case that an irregularity occurs, and etc.; and a display unit 160 for displaying as visible images the reflectance image and fluorescent-light image subjected to processing by the image processing unit 140.

The endoscope insertion portion 100 comprises a light guide 101 extending internally to the excitation light emitting end thereof, a CCD cable 102, and an image fiber 103. An illuminating lens 104 and an objective lens 105 are provided at the forward end of the light guide 101 and the CCD cable, that is, at the excitation light emitting end of the endoscope insertion portion 100. Further, the image fiber 103 is formed of composite glass fiber, and a focusing lens 106 and a excitation light cutoff filter 107 for cutting off light in the wavelength range below 420 nm, which is near the wavelength of the excitation light L2, from the fluorescent-light are provided at the forward end thereof. At the forward end of the CCD cable 102 is connected a CCD imaging element 108 with a color filter (not shown) mounted thereon, and a prism 109 is mounted on said CCD imaging element 108. The light guide 101 comprises a composite glass fiber white-light guide 101a and a fused quartz fiber excitation light guide 101b, which are bundled together and form an integrated cable; the white-light guide 101a and the excitation light guide 101b are connected to the illuminating unit 110. One end of the CCD cable 102 is connected to the image processing unit 140, and one end of the image fiber 103 is connected to the fluorescent-light image forming unit 130.

The illuminating unit 110 comprises a white-light source 111 that emits white-light L1 for obtaining standard and IR reflection-light images and a white-light source drive circuit 112 for supplying drive-current to said white-light source 111, a GaN semiconductor laser 115 that emits excitation light L2 for obtaining fluorescent-light images and a semiconductor-laser use drive circuit 114 for supplying drive-current to said GaN semiconductor laser, a transmissive mirror 117 with reflectance of several % for extracting a portion of the output emitted from the GaN semiconductor laser, a photo-detector 118 for detecting the excitation light emission-output P1 reflected by said transmissive mirror 117 and outputting the detection result to the irregularity controlling portion 152 of the control unit 150.

The image obtaining unit 120 comprises a switching filter 122 formed of a combination of three types of optical filters, a filter rotating unit 124 for rotating said switching filter 122, a CCD imaging element 125 for obtaining a fluorescent-light image transmitted by the switching filter 122 or an IR reflected-light image passed through the optical lens 129, an A/D converting circuit 126 for digitizing a signal obtained by said CCD photographing element 125, and an image memory 127 for storing an image signal that has been digitized by the A/D converting circuit 126.

Figure 2:
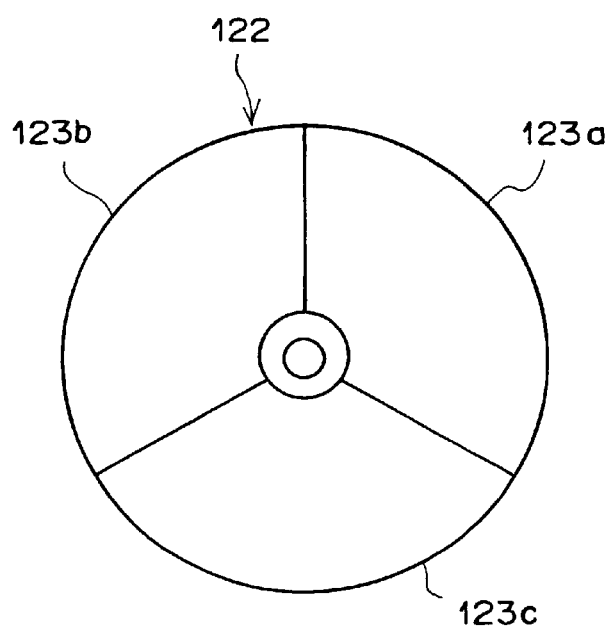
FIG. 2 is a drawing of a type of the switching filter employed in the fluorescence endoscope apparatus of the first embodiment.

The switching filter 122, as shown in FIG. 2, comprises an optical filter 123a, which is a band-pass filter for passing light having a wavelength in the 430–730 nm wavelength range, an optical filter 123b, which is a band-pass filter for passing light having a wavelength of 480 nm ±50 nm, and an optical filter 123c, which is a band-pass filter for passing light having a wavelength in the 750–900 nm wavelength range, such as those shown in FIG. 2: the optical filter 123a is a wide-band fluorescent-light image use optical filter; the optical filter 123b is a narrow-band fluorescent-light image use optical filter; and the optical filter 123c is an optical filter for use in IR reflected-light imaging. The switching filter 122 is controlled via the filter rotating unit 124, which is under the control of the main controlling portion 151, so that, when the white-light L1 is emitted, the optical filter 123c is disposed above the optical path, and when the excitation light L2 is emitted, the optical filter 123a and the optical filter 123b are disposed, alternately, over the optic path.

The image memory 127 comprises a narrow-band fluorescent-light image memory zone, a wide-band fluorescent-light image memory zone, and an IR reflected-light image memory zone (not shown). The narrow-band fluorescent-light image obtained when the target subject is irradiated by the excitation light L2 and in a state in which the narrow-band fluorescent-light imaging optical filter 123a is disposed above the optical path is stored in the narrow-band fluorescent-light image memory zone, and the wide-band fluorescent-light image obtained when the target subject is irradiated by the excitation light L2 and in a state in which the wide-band fluorescent-light imaging optical filter 123b is disposed above the optical path is stored in the wide-band fluorescent-light image memory zone. Further, the IR reflected-light image obtained when the target subject is illuminated with the white-light L1 and in a state in which the IR reflected-light imaging optical filter 123c is disposed above the optical path is stored in the IR reflected-light image memory zone.

The fluorescent light image composing unit 130 comprises a calculation portion 131 for determining a hue signal and which is provided with a prerecorded look-up table correlating the factor range between the fluorescent-light images and the hue H (Hue) occurring in the Munsell hue environment, a calculation portion 132 for determining a brightness signal and which is provided with a prerecorded look-up table correlating the pixel value range of an IR reflected-light image and a luminosity V (Value) occurring in the Munsell color system, and an image composing portion 133 for forming a fluorescent-light image based on both signals.

The image processing unit 140 comprises a signal processing circuit 141 for forming a reflectance image, which is a color image, from the signal obtained by the CCD imaging element 108, an A/D converting circuit 142 for digitizing the reflectance image obtained by said signal processing circuit 141, a reflectance image memory 143 for storing the digitized reflectance image, and a video signal processing circuit 144 for converting to a video image signal the reflectance image output from said reflectance image memory 143 and the fluorescent-light image composed by the image composing portion 133

The control unit 150 comprises a main controlling portion 151 and a irregularity controlling portion 152. The main controlling portion controls the timing of each unit during standard operations, and for cases in which the irregularity controlling portion 152 has received notification indicating that an irregularity has been detected, the drive current supplied to the GaN semiconductor laser 115 from the semiconductor-laser use drive circuit 114 is stopped, and the emission of the excitation light L2 is stopped and notification that an irregularity has occurred is displayed on the display unit 160.

The irregularity controlling portion 152 compares the excitation light emission-output P1 detected by the photodetector 118 provided in the illuminating unit 110 to a prerecorded setting value PS1, and for cases in which the excitation light emission-output P1 is larger than the setting value PS1, outputs an irregularity detection signal S1 to the main controlling portion 151.

The display unit 160 comprises a display 161 for displaying a reflectance image and a display 162 for displaying a fluorescent-light image.

Note that the GaN semiconductor laser 115 and the semiconductor-laser drive circuit 114 form the excitation light emitting means according to the present invention.

Hereinafter, the operation of a fluorescence endoscope of the configuration described above implementing the fluorescent-light image display apparatus according to the present invention will be explained. First, the operation occurring when a reflectance image and a fluorescent-light image are to be displayed will be explained, and then the operation occurring when an irregularity in the excitation light output has occurred will be explained.

According to the fluorescence endoscope apparatus of the current embodiment, the obtaining of a reflectance image and an IR reflected-light image and the obtaining of a fluorescent-light image are performed alternately at 1/60 seconds intervals every 1/30 seconds in a time division manner, and a reflectance image based on the reflectance image is displayed on the monitor 161 and a fluorescent-light image based on the fluorescent-light image is displayed on the monitor 162. Each image is displayed as a mobile image that is renewed every 1/30 seconds.

When a reflectance image and an IR reflected-light image are to be obtained, the white-light use power source 112 is driven based on a signal from the main controlling portion 151 and the white-light L1 is emitted from the white-light source 111. The white-light L1 enters the white-light guide 101a via the lens 113, and after being guided to the excitation light emitting end of the endoscope insertion portion, is projected onto the examination area of a target subject 1 by the illumination lens 104.

The reflected-light L4 of the white-light L1 is focused by the objective lens 105, reflected by the prism 109 and formed as an image by the CCD imaging element 108.

The signal processing circuit 141 forms a reflectance image, which is a color image, from the image signal obtained by the CCD photographing element 108. The reflectance image is input to the A/D converting circuit 142, and after being digitized, is stored in the reflectance image memory 143. The reflectance image stored in said reflectance image memory 143 is converted to a video signal by the video signal processing circuit 144, and then input to the display 161 and displayed thereon as a visible image. The series of operation described above is controlled by the main controlling portion 151.

On the other hand, the reflected-light L4 of the white-light L1 is focused by the focusing lens 106 and enters the forward end of the image fiber 103. The reflected-light L4 of the white-light L1 passes through the image fiber 103 and is focused by the lens 128, and is transmitted by the optical filter 123c of the switching filter 122.

Because the optical filter 123c is a band-pass filter that transmits only light having a wavelength within the wavelength range of 750–900 nm, the reflected-light image transmitted by the optical filter 123c becomes an IR reflected-light image formed only of the transmitted near-infrared wavelength range of light contained in the reflected-light L4.

This IR reflected-light image is received by the CCD imaging element 125. After the IR reflected-light image photoelectrically converted by the CCD photographing element 125 has been digitized by the A/D converting circuit 126, said IR reflected-light image is stored in the IR reflected-light image storage zone of the image memory 127.

Next, the operation occurring when a fluorescent-light image is obtained will be explained. The semiconductor-laser use drive circuit 114 is activated based on a signal from the main controlling portion 151, and excitation light L2 having a wavelength of 410 nm is emitted from the GaN semiconductor laser 115. The excitation light L2 is transmitted by the lens 116 and enters the excitation light guide 101b, and after being guided to the excitation light emitting end of the endoscope insertion portion, the excitation light L2 is projected onto the target subject 1 by the illuminating lens 104.

The fluorescent-light L3 emitted from the target subject upon irradiation thereof by the excitation light L2 is focused by the focusing lens 106, transmitted by the excitation light cutoff filter 107 and enters the forward end of the image fiber 103, focused by the lens 128 after passing through the image fiber 103, and is transmitted by the optical filter 123a or 123b of the switching filter 122.

The optical filter 123a is band-pass filter that transmits only light having a wavelength within the 430–730 nm wavelength range, and the light transmitted by the optical filter 123b becomes a wide-band fluorescent-light image. The optical filter 123b is band-pass filter that transmits only light having a wavelength of 480±50 nm wavelength range, and the light transmitted by the optical filter 123b becomes a narrow-band fluorescent-light image.

The wide-band fluorescent-light image and the narrow-band fluorescent-light image are received by the CCD imaging element 125, and after being photoelectrically converted by said CCD photographing element 125 and then digitized by the A/D converting circuit 144, the wide-band fluorescent-light image and the narrow-band fluorescent-light image are stored in the wide-band fluorescent-light image storage zone and the narrow-band fluorescent-light image storage zone, respectively, of the image memory 127.

Hereinafter, the operation occurring when a fluorescent-light image is to be formed will be explained. First, the calculating portion 131 of the fluorescent-light image forming unit 130 divides, for each pixel, the signal value occurring in the narrow-band fluorescent-light image stored in the narrow-band fluorescent-light image storage zone of the image memory 127 by the signal value occurring in the wide-band fluorescent-light image stored in the wide-band fluorescent-light image storage zone of the image memory 127; using a prerecorded look-up table and the factor obtained thereby, a hue H (Hue) occurring in the Munsell color specification system is determined and out put as a hue signal to the image composing portion 133.

The calculating portion 132 determines, for each pixel of an IR reflected light image stored in the IR reflected light image storage zone of image memory 127, a luminosity value V according to the Munsell color specification system using signal intensity and a look up table, and outputs said value as a luminosity signal to image composing section 133.

The image composing portion 133 forms a fluorescent-light image based on the hue H and the luminosity V obtained by the calculation portion 132. Note that for cases in which the image is to be displayed as a color image, the three color properties hue, luminosity, and saturation are required, so when an image is to be composed, the largest value of each hue and each luminosity is set as the saturation value.

Afterwards, an RGB conversion is performed, a fluorescent-light image is formed and output to the video signal processing circuit 144.

The fluorescent-light image converted to a video signal by the video signal processing circuit 144 is input to the display 162 and displayed thereon as a visible image. The series of operation described above is controlled by the main controlling portion 151.

Figure 3:
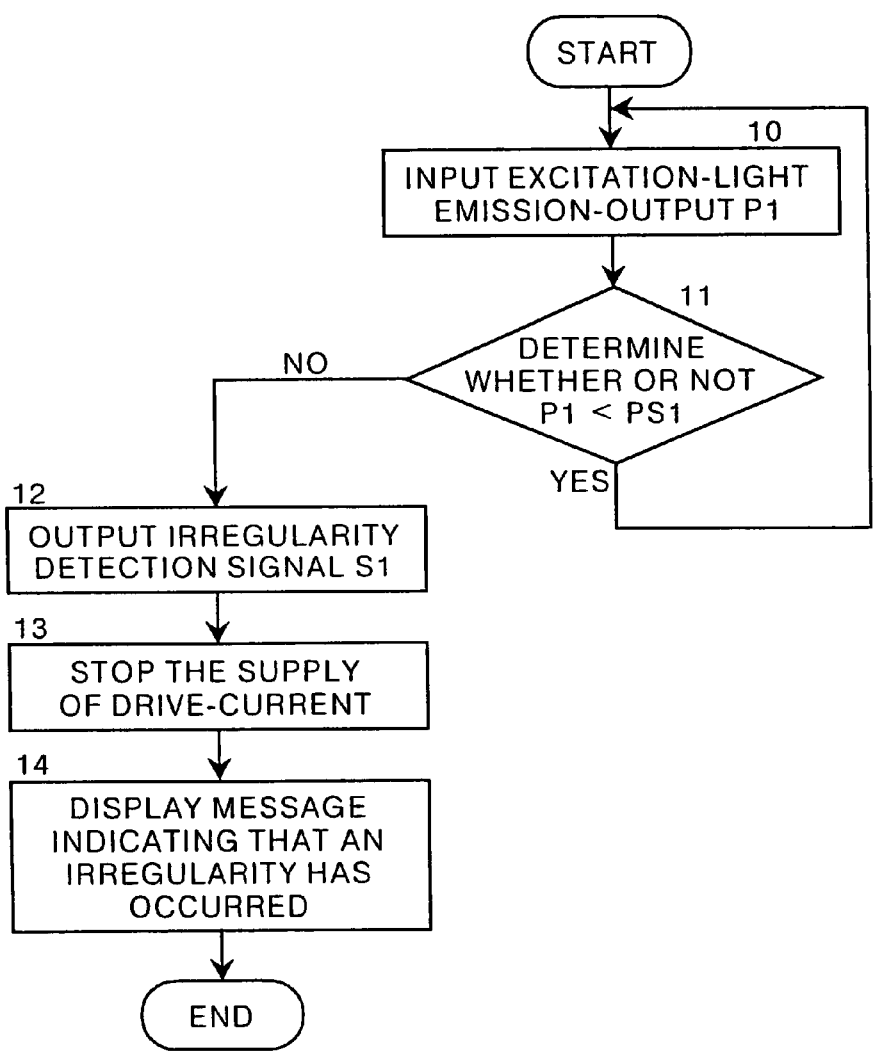
FIG. 3 is a flowchart of the operation of the fluorescence endoscope apparatus of the first embodiment of the present invention.

Next, using the flowchart shown in FIG. 3, a detailed explanation of the operation occurring when an irregularity occurs will be explained.

In step 10, the irregularity controlling portion 152 inputs at predetermined intervals the excitation light emission-output P1 detected by the photo-detector 118, and in step 11, the irregularity controlling portion 152 determines whether or not the detected excitation light emission-output P1 is smaller than a setting value PS1 that has been set therein. For cases in which the excitation light emission-output P1 is smaller than the setting value PS1, step 10 is returned to and repeated at predetermined intervals.

If the excitation light emission-output P1 is determined to be larger than the setting value PS1, step 12 is proceeded to, and for cases in which an irregular increase in the output of the excitation light has occurred, the irregularity detection signal S1 is output to the main controlling portion 151.

In step 13, the main controlling portion 151 stops the drive-current from being supplied to the GaN semiconductor laser 115, and stops the excitation light L2 from being projected onto the examination area of target subject 1.

In step 14, the main controlling portion 151 displays a message, on the display 162 that had been displaying a fluorescent-light image, indicating that an irregularity in the output of the excitation light has occurred, and that the emission of the excitation light L2 has therefore been stopped as well as the display of the fluorescent-light image.

Note that steps 10 through 12 form the emission-output detecting means, step 13 forms the drive stopping means, and step 14 forms the irregularity notification means according to the present invention.

According to the operation described above, for cases in which the output of the excitation light is greater than a predetermined value, because the supply of drive-current to the GaN semiconductor laser is stopped, the emission of the excitation light L2 can be reliably stopped and the examination area of a target subject 1 is not irradiated by excitation light having an energy density higher than a predetermined value, whereby safety is improved.

In addition, for cases in which the output of the excitation light L2 has become greater than a predetermined value, because a message indicative thereof is displayed on the display 162, an operator can immediately take appropriate measures, whereby the degree of safety is improved a level.

Note that although monitoring of the output of the excitation light has been conducted by use of the photoconductor 118 to detect the excitation light emission-output reflected from the transmissive mirror 117, the current embodiment is not limited to being of such a configuration; for example, a portion of the excitation light L2 emitted from the excitation light guide 101a can be reflected, and said reflected output can be detected.

Figure 4:
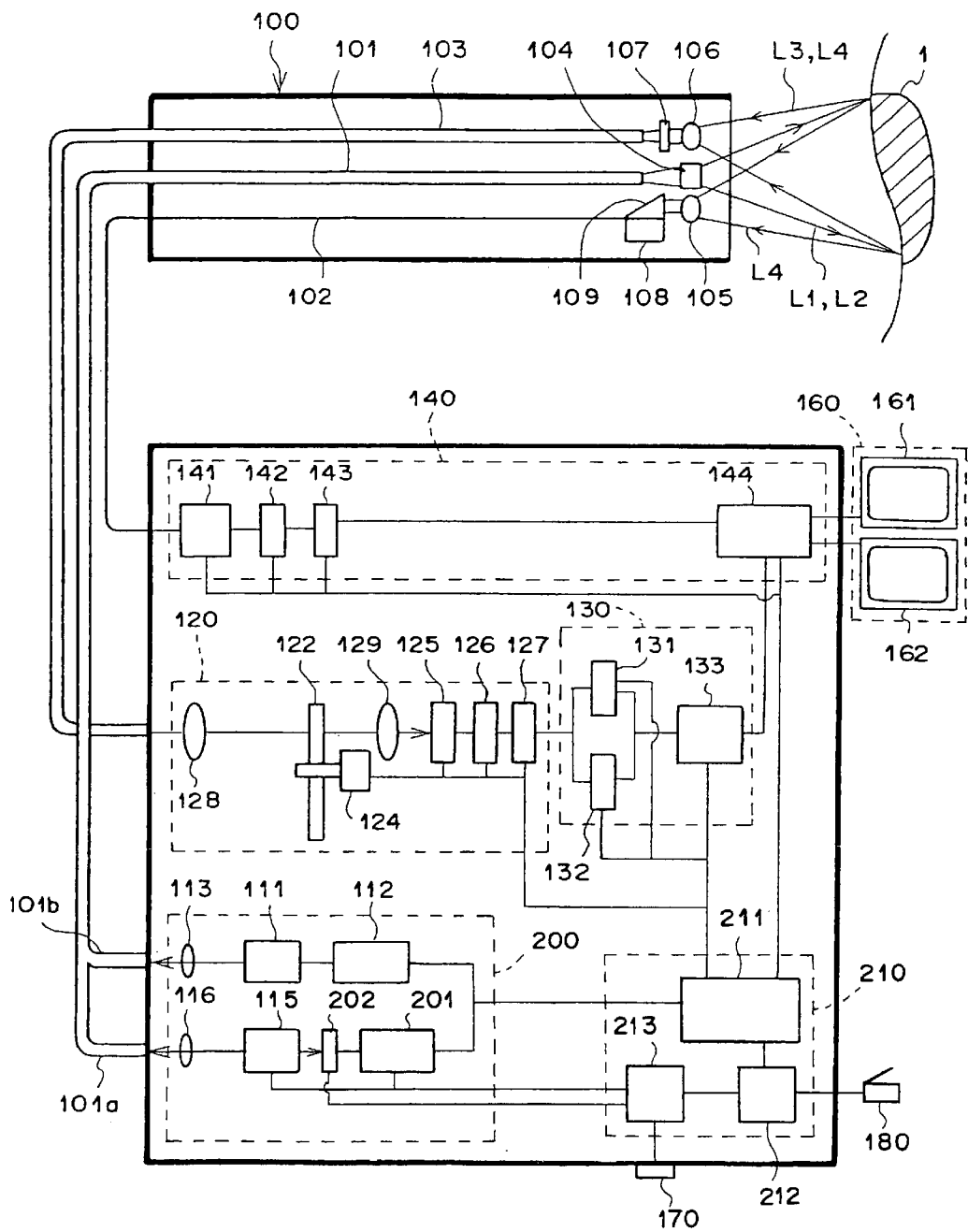
FIG. 4 is a schematic drawing of the second embodiment of a fluorescence endoscope apparatus implementing the fluorescent-light image display apparatus according to the present invention.

Next, with reference to FIG. 4, the second embodiment of a fluorescence endoscope apparatus implementing the fluorescent-light image display apparatus according to the present invention will be explained. FIG. 4 is a schematic drawing of the second embodiment of a fluorescence endoscope apparatus implementing the fluorescent-light image display apparatus according to the present invention. Elements that are the same as those of the first embodiment shown in FIG. 1 are likewise labeled, and in so far as further explanation thereof is not particularly necessary, it has been omitted.

According to the fluorescence endoscope apparatus of the current embodiment, a reflectance image viewing mode, in which a reflectance image is obtained and displayed on the reflectance image display 161, and a fluorescent-light image viewing mode, in which a fluorescent-light image and an IR reflected-light image are obtained and displayed on the fluorescent-light image display 162, are provided for performing viewing and examining of images: in the fluorescent-light image viewing mode, the excitation light emission-output P2 of the GaN semiconductor laser 115, which is emitted toward the rear direction and which is the emitted light having an output corresponding to the output of the excitation light L2, and the drive-current supplied to the GaN semiconductor laser 115 are monitored regularly. For cases in which the excitation light emission-output P2 of the excitation light L2 emitted toward the rear direction or the drive-current is above a predetermined value, the emission of the excitation light L2 is stopped and notification indicative thereof is provided, and the viewing mode is automatically switched from the fluorescent-light image viewing mode to the reflectance image viewing mode.

The fluorescence endoscope apparatus according to the second embodiment of the present invention comprises: an endoscope insertion portion 100 to be inserted into the body of a patient to a position near the location of the primary nidus and areas of suspected secondary infection; an illuminating unit 200 provided with a light source that emits white-light L1 for obtaining standard and IR reflection-light images and excitation light L2 for obtaining fluorescent-light images; an image obtaining unit 120 for obtaining two types of fluorescent-light images of different wavelength ranges and an IR reflected-light image; a fluorescent-light image forming unit 130 for forming a fluorescent-light image; an image processing unit 140 for performing image processing; a control unit 210 for controlling the operation timing, the timing occurring when an irregularity occurs, the viewing mode, and etc.; a display unit 160 for displaying as a visible image the reflectance image or the fluorescent-light image subjected to processing by the image processing unit 140; a buzzer 170; and a footswitch 180.

The illuminating unit 200 comprises a white-light source 111 that emits white-light L1 for obtaining standard and IR reflected-light images and a white-light source drive circuit 112 for supplying drive-current to said white-light source 111, a GaN semiconductor laser 115 that emits excitation light L2 for obtaining fluorescent-light images and a semiconductor-laser use drive circuit 201 for supplying drive-current to said GaN semiconductor laser, and a photo-detector 202 for measuring the excitation light emission-output P2, which is emitted toward the rear direction of the GaN semiconductor laser and outputting a measurement value to the drive circuit 201 and the irregularity controlling portion 213 of the control unit 210 described below.

The semiconductor-laser use drive circuit 201 is provided with an automatic power-control function for controlling the drive-current so that the excitation light emission-output P2, which is emitted toward the rear direction of the GaN semiconductor laser, measured by the photo-detector 202 is of a predetermined value that has been set in advance. Further, a drive-current value A1 is output to the irregularity controlling portion 213 of the control unit 210 described below.

The control unit 210 comprises a main controlling portion 211 and an irregularity controlling portion 212. The main controlling portion 211 is connected to each unit, the viewing mode switching portion 212, and the irregularity controlling portion 213.

The footswitch 180 and irregularity controlling portion 213 are connected to the viewing mode switching portion 212, and when the footswitch is depressed by an operator or an irregularity detection signal S2, which is described below, is input, the viewing mode switching portion outputs a mode switching signal for switching the viewing mode to the main controlling portion 210.

The irregularity controlling portion 213 compares the excitation light emission-output P2, which is emitted toward the rear direction of the GaN semiconductor laser and has been detected by the photo-detector 202 provided on the illumination unit 200, to a prerecorded setting value PS2, and also inputs the drive-current value A2 from the drive circuit 201 of the illumination unit 200 and compares said drive-current value to a prerecorded setting value AS2, and for cases in which the excitation light emission-output P2 is larger than the setting value PS2 and for cases in which the drive-current value A2 is larger than the setting value AS2, an irregularity detection signal S2 is output to the viewing mode switching portion 212 and the buzzer 170.

The main controlling portion 211 is connected to each unit, and operates in the reflectance image viewing mode, in which a reflectance image is displayed, and the fluorescent-light image viewing mode, in which a fluorescent-light image is displayed. When a mode switching signal is input to the main controlling portion from the viewing mode switching portion 212: for cases in which the apparatus is operating in the reflectance image viewing mode, the fluorescent-light image viewing mode is switched to; and for cases in which the apparatus is operating in the fluorescent-light image viewing mode, the reflectance image mode is switched to. In the reflectance image viewing mode, by stopping the drive-current from being supplied to the GaN semiconductor laser from the drive circuit 201, the emission of the excitation light L2 is stopped and only white-light L1 is projected onto the target subject 1, and a reflectance image is obtained.

Note that the GaN semiconductor laser 115 and the semiconductor-laser use drive circuit 201 form the excitation light emitting means according to the present invention; more particularly, the GaN semiconductor laser forms the excitation light source, and the semiconductor-laser use drive circuit forms the driving means.

Figure 5:
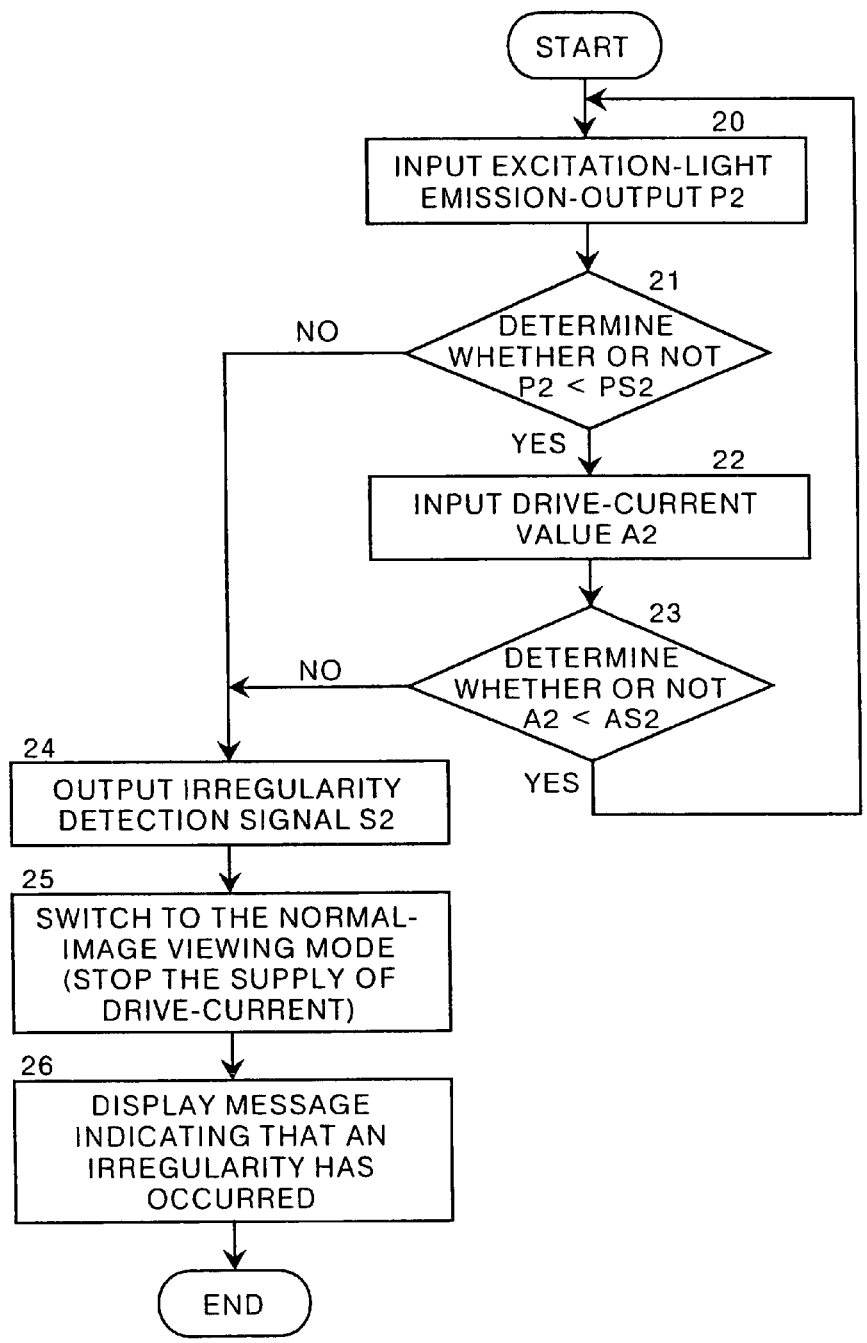
FIG. 5 is a flowchart of the operation of the fluorescence endoscope apparatus of the second embodiment of the present invention.

Hereinafter, the operation of the fluorescence endoscope apparatus according to the current embodiment will be explained. The operation occurring when a reflectance image is to be displayed and when a fluorescent-light image is to be displayed is performed by switching the viewing mode between a reflectance image viewing mode, in which only a reflectance image is displayed, and a fluorescent-light image viewing mode, in which only a fluorescent-light image is displayed, and the semiconductor-laser use drive circuit 201 is provided with an automatic power-control function for controlling the drive-current so that the excitation light emission-output P2, which is emitted toward the rear direction of the GaN semiconductor laser, measured by the photo-detector 202 is of a predetermined value that has been set in advance. Because other operations are the same as those of the first embodiment shown in FIG. 1, further explanation thereof has been omitted; a detailed explanation of the operation which occurs when an irregularity occurs will be given, using the flowchart shown in FIG. 5.

In step 20, the irregularity controlling portion 213 inputs the excitation light emission-output P2, which is emitted toward the rear direction of the GaN semiconductor laser, measured by the photo-detector 202, and in step 21, the irregularity controlling portion 213 determines whether or not said excitation light emission-output P2 is smaller than the preset value PS2 recorded in the irregularity controlling portion 213; if the excitation light emission-output P2 is determined to be smaller than the setting value PS2, step 22 is proceeded to. In step 22, the drive-current value A1 from the drive circuit 201 is input to the irregularity controlling portion 213, and in step 23, the irregularity controlling portion 213 determines whether or not the drive-current value A2 is smaller than the preset value AS2 recorded in the irregularity controlling portion 213; if the drive-current value A2 is determined to be smaller than the setting value AS2, step 20 is returned to and repeated at predetermined intervals.

In step 21, if the excitation light emission-output P2 is determined to be greater than the setting value PS2, it is recognized that an irregular increase in the output of the excitation light has occurred and step 24 is proceeded to, and an irregularity detection signal S2 is output to the viewing mode switching portion 212. Further, in step 23, if the drive-current value A2 is determined to be greater than the setting value AS2, it is recognized that an irregular increase in the output of the excitation light has occurred and step 24 is proceeded to, and an irregularity detection signal S2 is output to the viewing mode switching portion 212 and to the buzzer 170.

In step 25, the viewing mode switching portion 212 outputs a viewing mode switching signal to the main controlling portion 211, and the main controlling portion 211 switches the viewing mode from the fluorescent-light image viewing mode to the reflectance image viewing mode. At this point, the supply of drive-current to the GaN semiconductor laser is stopped, and the emission of the excitation light is stopped.

In step 26, the buzzer 170 emits a warning sound indicating to the operator that an irregular increase in the output of the excitation light L2 has occurred.

Note that steps 20–24 form the irregularity detecting means according to the present invention; more particularly, steps 20, 21, and 24 form the emission-output detecting means, and steps 22, 23 and 24 form the drive-current detecting means. Further, step 25 forms the reflectance image viewing mode setting means and the drive stopping means according to the present invention. Still further, step 26 forms the irregularity notification means according to the present invention.

According to the operation described above, for cases in which the output of the excitation light is greater than a predetermined value, because the supply of drive-current to the GaN semiconductor laser is stopped, the emission of the excitation light L2 can be reliably stopped and the target subject 1 is not irradiated by excitation light having an energy density higher than a predetermined value, whereby safety is improved.

In addition, for cases in which the excitation light emission-output has become greater than a predetermined value, because a warning sound is emitted by the buzzer, an operator can immediately take appropriate measures, whereby the degree of safety is improved a level.

Further, according to the current embodiment, because the detection of the occurrence of an irregularity is performed by monitoring both the excitation light emission-output emitted toward the rear direction of the GaN semiconductor laser 115 and the of drive-current supplied to the GaN semiconductor laser, for cases in which an irregularity occurs in the irregularity detecting means itself, even, for example, if an irregularity occurs in the photo-detector 202 and it becomes impossible to accurately measure the excitation light emission-output emitted toward the rear direction of the GaN semiconductor laser, an irregularity in the drive-current can be detected, and because the emission of the excitation light can be stopped, the safety of the patient can be ensured with a high degree of reliability.

Note that there are many cases for which the rate of occurrence of irregularities is low, and for such cases, a sufficient monitoring result can be obtained by supplying only one or the other of an emission-output detecting means for detecting that the excitation light emission-output emitted toward the rear direction of the GaN semiconductor laser 115 is greater than a predetermined value or a drive-current detecting means for detecting that the of drive-current supplied to the GaN semiconductor laser 115 is greater than a predetermined value.

Figure 6:
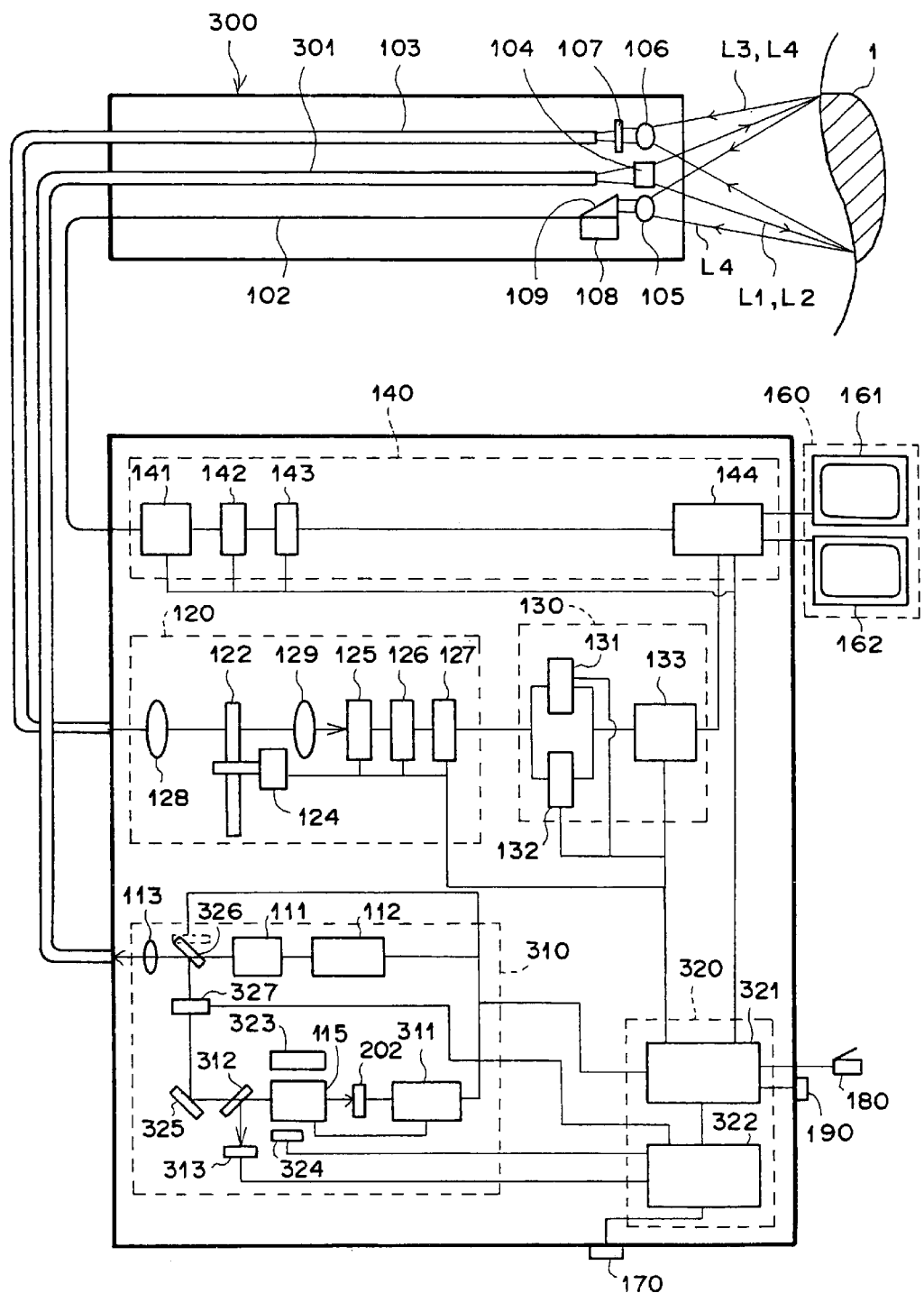
FIG. 6 is a schematic drawing of the third embodiment of a fluorescence endoscope apparatus implementing the fluorescent-light image display apparatus according to the present invention.

Next, the third embodiment of a fluorescence endoscope apparatus implementing the fluorescent-light image display apparatus according to the present invention will be explained with reference to FIG. 6. FIG. 6 is a schematic drawing of the third embodiment of a fluorescence endoscope apparatus implementing the fluorescent-light image display apparatus according to the present invention: elements that are the same as those of the second embodiment shown in FIG. 4 are likewise labeled, and in so far as there is no particular need for further explanation thereof, it has been omitted.

According to the current embodiment of a fluorescence endoscope apparatus implementing the fluorescent-light image display apparatus according to the present invention: viewing of images is provided for by a reflectance image viewing mode, in which a reflectance image is obtained and displayed on the display 161, and a fluorescent-light image viewing mode, in which a fluorescent-light image and an IR reflected-light image are obtained and a fluorescent-light image is displayed on the display 162; and in the fluorescent-light image viewing mode, the emission-output of the GaN semiconductor laser 115 and the temperature of the GaN semiconductor laser 115 are monitored at regular intervals. For cases in which the emission-output of the excitation light is greater than a predetermined value or the temperature of the GaN semiconductor laser 115 is lower than a predetermined value, the emission of the excitation light is stopped, notification thereof is provided to the operator, and the reflectance image viewing mode is automatically switched to.

The fluorescence endoscope apparatus according to the third embodiment of the present invention comprises: an endoscope insertion portion 300 to be inserted into the body of a patient to a position near the location of the primary nidus and areas of suspected secondary infection; an illuminating unit 310 provided with a light source that emits white-light L1 for obtaining standard IR reflected-light images and excitation light L2 for obtaining fluorescent-light images; an image obtaining unit 120 for obtaining two types of fluorescent-light images of different wavelength ranges and an IR reflected-light image; a fluorescent-light image forming unit 130 for forming a fluorescent-light image; an image processing unit 140 for performing image processing; a control unit 320 for controlling the operation timing, the timing occurring when an irregularity occurs, the viewing mode, and etc.; a display unit 160 for displaying as a visible image the reflectance image or the fluorescent-light image subjected to processing by the image processing unit 140; a buzzer 170; a footswitch 180; and an input operation portion 190. Note that elements that are the same as those of the second embodiment shown in FIG. 4 are likewise labeled, and in so far as there is no particular need for further explanation thereof, it has been omitted.

The endoscope insertion portion 300 comprises a light guide 301 extending internally to the excitation light emitting end thereof, a CCD cable 102 and an image fiber 103. The light guide 301 is a fused quartz fiber and is connected to the illuminating unit 310.

The illuminating unit 310 comprises a white-light source 111 that emits white-light L1 for obtaining standard and IR reflected-light images and a white-light source drive circuit 112 for supplying drive-current to said white-light source 111, a GaN semiconductor laser 115 that emits excitation light L2 for obtaining fluorescent-light images and a semiconductor-laser drive circuit 311 for supplying drive-current to said GaN semiconductor laser, a photo-detector 202 for measuring the excitation light emission-output P2, which is emitted toward the rear direction of the GaN semiconductor laser and outputting a measurement value to the drive circuit 311, a transmissive mirror 312 for extracting a portion of the output emitted from the GaN semiconductor laser 115, a photo-detector 313 for measuring the excitation light emission-output P3 reflected by said transmissive mirror 312 and outputting the detection result to the irregularity controlling portion 322, a temperature regulating portion 323 for regulating the temperature of the GaN semiconductor laser to a predetermined temperature, a thermistor 324 for measuring the temperature T3 of the GaN semiconductor laser 115 and outputting the temperature T3 to the irregularity controlling portion 322, a mirror 325 for reflecting the excitation light L2 emitted from the GaN semiconductor laser 115, a movable mirror 326 that is disposed in the position shown by the broken line when the white-light L1 is to be made to enter the light guide 303 and disposed in the position shown by the solid line when the excitation light L2 is to be made to enter the light guide 303, and a shutter 327, which is normally maintained in the open state by the irregularity controlling portion 322, disposed between the mirror 325 and the mirror 326.

The semiconductor-laser use drive circuit 311 is provided with an automatic power control function for controlling, via the main controlling portion 321 described below, the drive-current so that the estimated emission-output of the excitation light L2, which has been estimated from the excitation light emission-output emitted toward the rear direction of the GaN semiconductor laser 115 measured by the photo-detector 202, so that said estimated emission-output of the excitation light L2 conforms to the setting value PS3 set at the input operation portion 190.

The temperature regulating portion 323 detects the temperature of the GaN semiconductor laser 115 by use of an internal thermistor, and cools the GaN semiconductor laser 115, by use of a Peltier element, so that the temperature thereof is maintained within a predetermined range.

The rotating mirror 326, under the control of the main controlling portion 321, is disposed in the position indicated by the broken line when a reflectance image or an IR reflected-light image is to be obtained, whereby the white-light L1 is made to enter the light guide 303; when a fluorescent-light image is to be obtained, said rotating mirror 326 is disposed in the position indicated by the solid line, and the excitation light L2 is made to enter the light guide 303.

The shutter 327 is normally maintained in an open position in which it does not block the optical path of the excitation light L2, however, when an irregularity detection signal S3 is output from the irregularity controlling means 322, it moves to the closed position, whereby the optical path of the excitation light L2 is cut off.

The control unit 320 comprises a main controlling portion 321 and an irregularity controlling portion 322. The main controlling portion 321 is connected to each unit as well as to the foot switch 180 and the input operation portion 190, and controls the operation timing of each unit when a reflectance image is to be obtained; if the footswitch 180 is depressed by an operator, the viewing mode is switched from the reflectance image viewing mode to the fluorescent-light image viewing mode or from the fluorescent-light image viewing mode to the reflectance image viewing mode.

In addition, in the fluorescent-light image viewing mode, for cases in which an irregularity detection signal S3 is output from the irregularity detecting portion 322, the supply of drive-current from the semiconductor-laser use drive circuit 311 to the GaN semiconductor laser 115 is stopped, the emission of the excitation light L2 is stopped, and the viewing mode is switched from the fluorescent-light image viewing mode to the reflectance image viewing mode.

Note that in the fluorescent-light image viewing mode, the emission output of excitation light L2 which is input at the input operation portion 190 by an input operation is output by the main controlling portion to the drive circuit 311 and the irregularity controlling portion 322. An operator sets the setting value PS 3 so that the energy density of the excitation light L2 projected onto the examination area of a target subject 1 does not exceed an MPE value.

The irregularity controlling portion 322 computes, based on the transmissivity index of the transmissive mirror 312, the emission-output P3' of the excitation light L2 from the excitation light emission-output P3 detected by the photo-detector 313 provided on the illuminating unit 310, and compares the computed emission-output P3' to the setting value PS3+α output from the main controlling portion 321; for cases in which the emission-output P3' is greater than the setting value PS3+α, an irregularity detection signal S3 is output to the main controlling portion 321, the buzzer 170, and the shutter 327.

Furthermore, even for cases in which the temperature T3 of the GaN semiconductor laser 115 measured at the same time by the thermistor 313 is lower than the predetermined value ST3 that has been set in advance, the irregularity controlling portion 322 outputs an irregularity detection signal S3 to the main controlling portion 321, the buzzer 170, and the shutter 327.

Note that the GaN semiconductor laser 115, the semiconductor-laser drive circuit 311, the photo-detector 202 and the temperature regulating portion 323 form the excitation light emitting means of the current embodiment according to the present invention; more particularly, the GaN semiconductor laser 115 constitutes the excitation light source, the drive circuit 311 constitutes the driving means, and the temperature regulating portion 323 constitutes the temperature regulating means. Further, the main controlling portion 321 also serves as the viewing mode switching means according to the current embodiment of the present invention.

Figure 7:
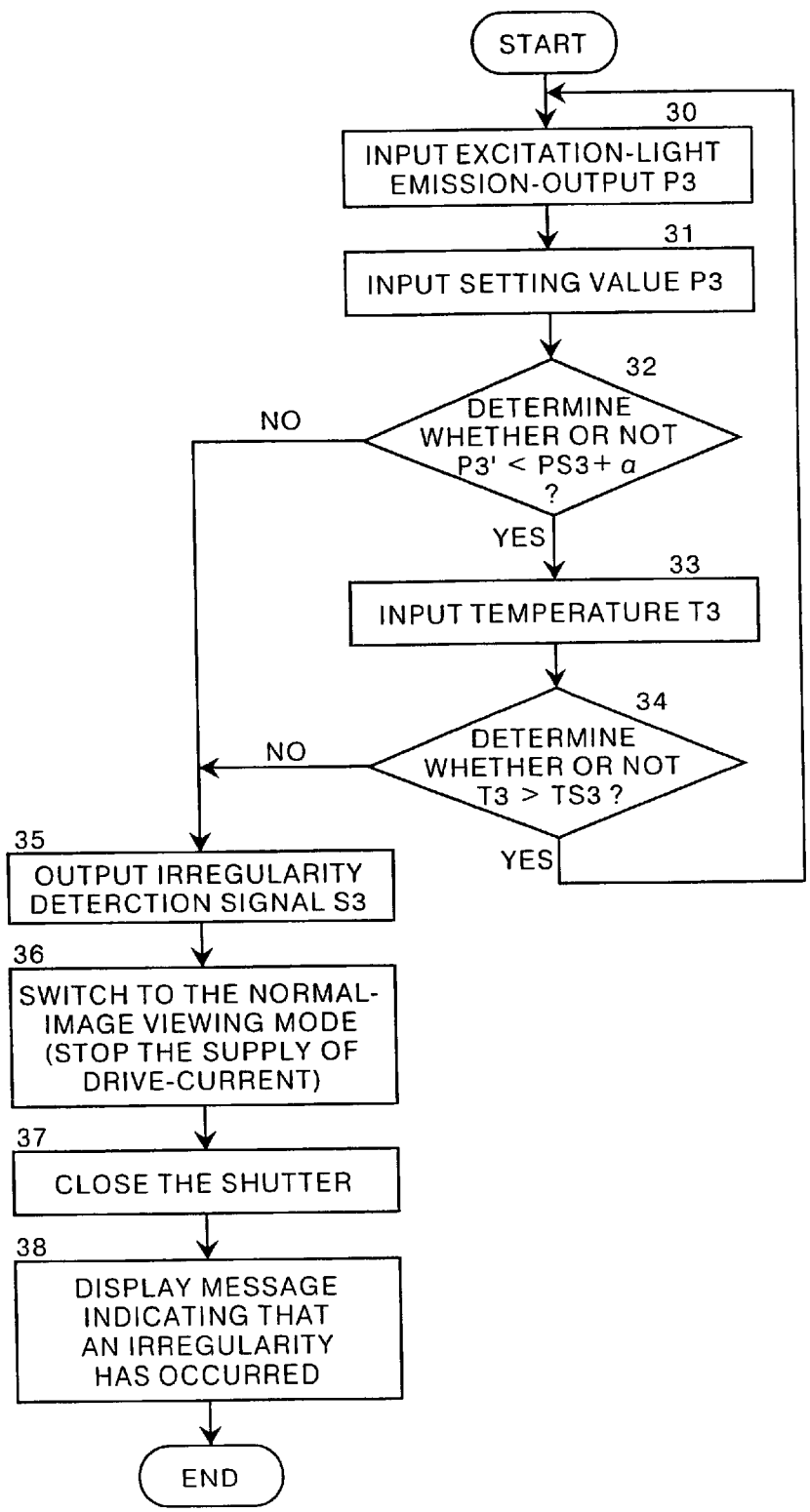
FIG. 7 is a flowchart of the operation of the operation of the fluorescence endoscope apparatus of the third embodiment of the present invention.

Next, the operation of the fluorescence endoscope apparatus according to the current embodiment will be explained. According to the operation which occurs when a reflectance image is to be displayed and the operation which occurs when a fluorescent-light image is to be displayed, the white-light L1 and the excitation light L2 are guided by a single light guide, not two; the emission output of the excitation light L2 is set by an input operation; the temperature of the GaN semiconductor laser is regulated by the temperature regulation portion 323 so as to be maintained within a predetermined range; because the other operations are the same as those occurring in the fluorescence endoscope apparatus according to the second embodiment, further explanation thereof has been omitted; and the operation which occurs when an irregularity occurs will be explained in detail, with reference to the flowchart shown in FIG. 7.

In step 30, the irregularity controlling portion 322 inputs the excitation light emission-output P3 from the photo-detector 313, and in step 31, the setting value PS3 is read out from the main controlling portion 312.

In step 32, the irregularity controlling portion 322 computes the emission-output P3' of the excitation light L2, based on the excitation light emission output P3 and the reflectivity index of the transmissive mirror 312, and determines whether or not the computed emission-output P3' is smaller than the setting value PS3+α. For cases in which the emission-output P3' is smaller than the setting value PS3+α, step 33 is proceeded to. In step 33, the irregularity controlling portion 322 inputs the temperature T3 of the GaN semiconductor laser from the thermistor 324, and in step 34, it is determined whether or not the temperature T3 is higher than the setting value ST3 prerecorded in the irregularity controlling portion 322. For cases in which the temperature T3 is determined to be higher than the setting value ST3, step 30 is returned to and repeated at predetermined intervals.

In step 32, if the emission-output P3' is determined to be greater than the setting value PS3+α, it is recognized that an irregular increase in the output of the excitation light L2 has occurred and step 33 is proceeded to, and an irregularity detection signal S3 is output to the main controlling portion 321 and the buzzer 170. Further, in step 34, if the temperature T3 is determined to be lower than the setting value ST3, it is recognized that an irregular increase in the output of the excitation light L2 has occurred and step 35 is proceeded to. That is to say, because the emission-output of the excitation light L2 decreases if the temperature of the GaN semiconductor laser 115 rises, a Peltier element is used in the temperature regulating portion 323 to cool the GaN semiconductor laser 115 so that the temperature thereof is maintained in a predetermined range. However, when an irregularity occurs in the temperature regulating portion 323 itself, for cases in which the GaN semiconductor laser 115 is excessively cooled, there is a possibility that the emission-output of the excitation light L2 will increase. Therefore, it is desirable that the emission of the excitation light L2 is stopped when the temperature T3 of the GaN semiconductor laser 115 is lower than the setting value TS3.

In step 36, the main controlling portion 321 switches the viewing mode from the fluorescent-light image viewing mode to the reflectance image viewing mode.

In step 37, the shutter 327 is shut so that it is in the closed state and the optical path of the excitation light L2 is blocked.

In step 38, a warning sound is emitted by the buzzer 170 to inform the operator that an irregularity has occurred in the emission of the excitation light L2.

Note that steps 30–35 form the irregularity detecting means according to the current embodiment of the present invention; more particularly, steps 30, 31, 32, and 35 form the emission-output detecting means, and steps 33, 34, and 35 form the temperature detecting means. Further, step 36 constitutes the reflectance image viewing mode setting means according to the current embodiment, step 37 the excitation light L2 optical path cutoff means, and step 38 the irregularity notification means.

According to the operation described above, when the emission-output P3', set at the input operation portion 190, is greater than the setting value PS3+α or the temperature T3 is lower than a predetermined value TS3, the optical path of the excitation light L2 is blocked by the shutter 327, thereby the emission of the excitation light L2 can be reliably stopped, the examination area of a target subject 1 is not irradiated with excitation light L2 having an energy density greater than a predetermined value, and safety is improved. Further, even for cases in which an irregularity occurs in the output of the excitation light L2 or in the temperature of the GaN semiconductor laser 115 because of some kind of irregularity occurring in the main controlling portion 321, because the shutter 327 blocks the optical path of the excitation light L2, the emission of the excitation light L2 can reliably be stopped.

In addition, for cases in which emission-output P3' is greater than the setting value PS3+α or the temperature T3 is lower than a predetermined value TS3, because a warning sound is emitted by the buzzer 170, an operator can immediately take appropriate measures, and safety is improved a level.

Further, according to the current embodiment, because both the emission-output P3 and the temperature T3 of the GaN semiconductor laser 115 are monitored for the detection of irregularities, even if an irregularity occurs in one or the other of the photo-detector 313 or the thermistor 324, if the other is functioning properly, an irregularity in the output of the excitation light L2 can be detected; because the emission of the excitation light L2 can reliably be stopped, the safety of the patient can reliably be ensured. Further, as an alternative version of the current embodiment, it is possible that a drive-current detecting means be further provided for monitoring the drive-current, whereby the reliability in detecting an irregularity in the output of the excitation light L2 can be improved a level.

Note that there are many cases for which the rate of occurrence of irregularities is low, and for such cases, a sufficient monitoring result can be obtained by supplying only one or the other of an emission-output detecting means for detecting that the emission-output P3' is greater than the setting value PS3+α or a temperature detecting means for detecting that the temperature T3 of the GaN semiconductor laser 115 is lower than a predetermined value TS3.

Note that monitoring of the emission-output of the excitation light L2 has been performed by using a photo-detector 313 to detect the excitation light emission-output P3 reflected by the transmissive mirror 312, however, the current embodiment is not limited to such a configuration; for example, a portion of the excitation light L2 emitted from the light guide 301 can be reflected, and the emission-output thereof can be detected.

In addition, as an alternative version of the current embodiment, instead of being performed regularly when in the fluorescent-light image viewing mode, the monitoring of the emission-output of the excitation light L2 can be performed only when the fluorescent-light image viewing mode is switched to. In this case, the transmissive mirror can be a movable mirror, and said transmissive mirror can be inserted into the optical path of the excitation light L2 only immediately after the viewing mode has been switched to the fluorescent-light image viewing mode and the emission-output of the excitation light L2 monitored. Because the transmissive mirror is withdrawn from the optical path when an image is being viewed, a transmissive mirror having a high reflectance index can be used, the quantity of the excitation light L2 that can be received by the photo-detector can be increased, and the emission-output of the excitation light can be accurately detected.

Note that according to each of the embodiments described above, by utilizing excitation light L2 having a wavelength in the 400–420 nm wavelength range, more reliable data of a target subject can be obtained. Further, by using a GaN semiconductor laser as the excitation light source, the size of the apparatus can be made compact and the cost reduced.

Note that according to each of the embodiments described above, it is conceivable that a self-check function be provided to the fluorescence endoscope apparatus in addition to each irregularity detecting means, for performing a self-check of the structural components of each unit. For example, by carrying out a self-check of the photo-detector, the shutter, the rotating mirror, the light-source driver, the CCD imaging element, or the temperature regulating portion, the reliability of the apparatus can be improved.

What is claimed is:

1. A fluorescent-light image display apparatus comprising:
   excitation light emitting means for emitting excitation light,
   illuminating-light emitting light means for emitting illuminating-light,
   fluorescent-light image obtaining means for obtaining an image formed by the fluorescent-light emitted from an examination area of a target subject upon the irradiation thereof by the excitation light,
   reflectance image obtaining means for obtaining a reflectance image formed by the reflected-light reflected from an examination area of a target subject upon the irradiation thereof by the illuminating-light, fluorescent-light image display means for displaying a fluorescent-light image based on the fluorescent-light image obtained by said fluorescent image obtaining means, and reflectance image displaying means for displaying a reflectance image based on the reflectance image obtained by said reflectance image obtaining means, wherein the excitation light emitting means is provided with an irregularity detecting means for detecting irregular increases occurring in the output of the excitation light, and excitation light emission stopping means for stopping the emission of the excitation light being projected onto an examination area of a target subject, according to the detection of an irregularity by the irregularity detecting means.

2. A fluorescent-light image display apparatus as defined in claim 1, further comprising switching means capable of switching, by use of an input operation, between a fluorescent-light image viewing mode, in which the excitation light is projected onto examination area of a target subject and a fluorescent-light image obtained, said fluorescent light image being displayed, and a reflectance image viewing mode, in which the illuminating-light is projected onto an examination area of a target subject and a reflectance image obtained, said reflectance image then being displayed, and reflectance image viewing mode setting means for switching from the fluorescent-light image viewing mode to the reflectance image viewing mode when an irregularity is detected by the irregularity detecting means while the apparatus is in the fluorescent-light image viewing mode.

3. A fluorescent-light image display apparatus as defined in claim 1, further comprising an irregularity notification means for providing notification, upon detection by the irregularity detecting means of an irregularity, that an irregularity has been detected.

4. A fluorescent-light image display apparatus as defined in claim 2, further comprising an irregularity notification means for providing notification, upon detection by the irregularity detecting means of an irregularity, that an irregularity has been detected.

5. A fluorescent-light image display apparatus as defined in claims 1, 2, 3 or 4, wherein said irregularity detecting means is provided with an emission-output detecting means for detecting that the excitation light emitted by the excitation light emitting means or the output of the emitted light corresponding to the output of the excitation light is larger than a predetermined value.

6. A fluorescent-light image display apparatus as defined in claims 1, 2, 3, or 4, wherein the excitation light emitting means is provided with a excitation light source for producing excitation light and driving means for providing an electric drive-current to said excitation light source, and the irregularity detecting means is provided with a drive-current detecting means for detecting that the drive-current is greater than a predetermined value.

7. A fluorescent-light image display apparatus as defined in claims 1, 2, 3, or 4, wherein the excitation light emitting means is provided with a excitation light source that increases the output of the excitation light as the temperature decreases and a temperature regulating means for adjusting the temperature of said excitation light source, and the irregularity detecting means is provided with a temperature detecting means for detecting that the temperature is lower than a predetermined value.

8. A fluorescent-light image display apparatus as defined in claim 1, 2, 3, or 4, wherein the excitation light emitting means is provided with a excitation light source for producing excitation light and driving means for providing an electric drive-current to said excitation light source, and the irregularity detecting means is provided with a drive-current detecting means for detecting that the drive-current is greater than a predetermined value, and the irregularity detecting means is provided with an emission-output detecting means for detecting that the excitation light emitted by the excitation light emitting means or the output of the emitted light corresponding to the output of the excitation light is larger than a predetermined value.

9. A fluorescent-light image display apparatus as defined in claim 1, 2, 3, or 4, wherein the excitation light emitting means is provided with a excitation light source for producing excitation light and driving means for providing an electric drive-current to said excitation light source, and the irregularity detecting means is provided with a drive-current detecting means for detecting that the drive-current is greater than a predetermined value, and the excitation light emitting means is provided with a excitation light source that increases the output of the excitation light as the temperature decreases and a temperature regulating means for adjusting the temperature of said excitation light source, and the irregularity detecting means is provided with a temperature detecting means for detecting that the temperature is lower than a predetermined value.

10. A fluorescent-light image display apparatus as defined in claims 1, 2, 3, or 4, wherein the excitation light emitting means is provided with a excitation light source that increases the output of the excitation light as the temperature decreases and a temperature regulating means for adjusting the temperature of said excitation light source, and the irregularity detecting means is provided with a temperature detecting means for detecting that the temperature is lower than a predetermined value, and the irregularity detecting means is provided with an emission-output detecting means for detecting that the excitation light emitted by the excitation light emitting means or the output of the emitted light corresponding to the output of the excitation light is larger than a predetermined value.

11. A fluorescent-light image display apparatus as defined in claims 1, 2, 3, or 4, wherein the excitation light emitting means is provided with a excitation light source for producing excitation light and driving means for providing an electric drive-current to said excitation light source, and the irregularity detecting means is provided with a drive-current detecting means for detecting that the drive-current is greater than a predetermined value, and the excitation light emitting means is provided with a excitation light source that increases the output of the excitation light as the temperature decreases and a temperature regulating means for adjusting the temperature of said excitation light source, and the irregularity detecting means is provided with a temperature detecting means for detecting that the temperature is lower than a predetermined value, and the irregularity detecting means is provided with an emission-output detecting means for detecting that the excitation light emitted by the excitation light emitting means or the output of the emitted light corresponding to the output of the excitation light is larger than a predetermined value.

12. A fluorescent-light image display apparatus as defined in claims 1, 2, 3, or 4, wherein the excitation light emitting means is provided with a excitation light source for producing excitation light and driving means for providing electric drive-current to said excitation light source, and the excitation light emission stopping means is provided with a drive stopping means for stopping the supply of drive-current to the excitation light source.

13. A fluorescent-light image display apparatus as defined in claim 1, 2, 3, or 4, wherein the excitation light emission stopping means is a means provided with an optical path cutoff means for cutting off the optical path between the excitation light emitting means and an examination area of a target subject.

14. A fluorescent-light image display apparatus as defined in claims 1, 2, 3, or 4, wherein the wavelength of the excitation light is in the 400–420 nm range.

15. A fluorescent-light image display apparatus as defined in claims 1, 2, 3, or 4, wherein the excitation light source is a semiconductor laser.

16. A fluorescent-light image display apparatus as defined in claim 15, wherein the semiconductor laser is a GaN semiconductor laser.

* * * * *